United States Patent [19]
Spetzler

[11] Patent Number: 5,669,912
[45] Date of Patent: Sep. 23, 1997

[54] APPARATUS FOR SECURING A CRANIAL PIECE IN POSITION

[76] Inventor: Robert F. Spetzler, 6107 N. Palo Cristi, Paradise Valley, Ariz. 85253

[21] Appl. No.: 518,103

[22] Filed: Aug. 22, 1995

Related U.S. Application Data

[63] Continuation of Ser. No. 233,851, Apr. 26, 1994, Pat. No. 5,501,685.

[51] Int. Cl.⁶ .................................................. A61B 17/56
[52] U.S. Cl. ........................... 606/72; 606/75; 606/104; 606/86
[58] Field of Search ........................ 606/67, 60, 72, 606/75, 86, 99, 104, 205, 207; 623/16; 411/458, 460, 487, 493–499

[56] References Cited

U.S. PATENT DOCUMENTS

| | | | |
|---|---|---|---|
| 827,392 | 7/1906 | Pragemeier | 81/426.5 |
| 1,189,998 | 7/1916 | Perkins. | |
| 1,710,891 | 4/1929 | O'Hare | 411/458 |
| 2,672,861 | 3/1954 | Jonas et al. | 128/92 |
| 3,693,496 | 9/1972 | Koide. | |
| 4,516,569 | 5/1985 | Evans et al. | 128/92 |
| 4,554,914 | 11/1985 | Kapp et al. | 128/92 |
| 4,629,463 | 12/1986 | Grundei et al. | 623/16 |
| 4,858,601 | 8/1989 | Glisson | 128/92 |
| 4,858,603 | 8/1989 | Clemon et al. | |
| 4,938,768 | 7/1990 | Wu | 606/60 |
| 5,207,712 | 5/1993 | Cohen | 606/60 |
| 5,257,995 | 11/1993 | Umber et al. | 606/99 |
| 5,380,338 | 1/1995 | Christian | 606/205 |

FOREIGN PATENT DOCUMENTS

| | | | |
|---|---|---|---|
| 1392574 | 2/1965 | France | 411/458 |
| 4114657 | 4/1992 | Japan | 623/16 |

Primary Examiner—Michael Buiz
Assistant Examiner—Mark S. Leonardo
Attorney, Agent, or Firm—Cahill, Sutton & Thomas P.L.C.

[57] ABSTRACT

A device for securing a previously removed cranial plate in position in a cranium to prevent relative movement between opposing bone edges includes a pin containing distal and proximal shanks having ends tapering to a relatively sharp point. The shanks are arranged preferably symmetrically about a central collar which has a dimension transverse to the longitudinal axis of the shanks greater than the diameters of the shanks so that the collar forms distal and proximal opposing shoulders for limiting the insertion depth of the pin.

8 Claims, 3 Drawing Sheets

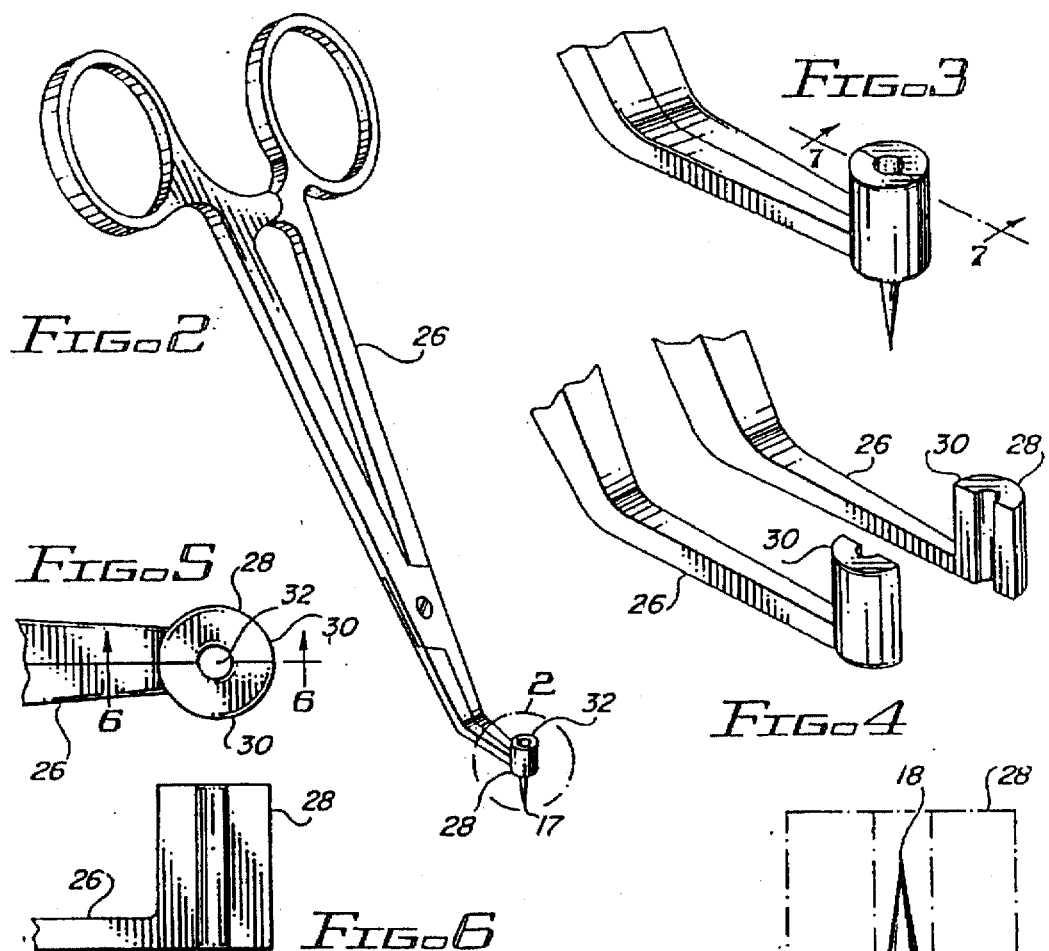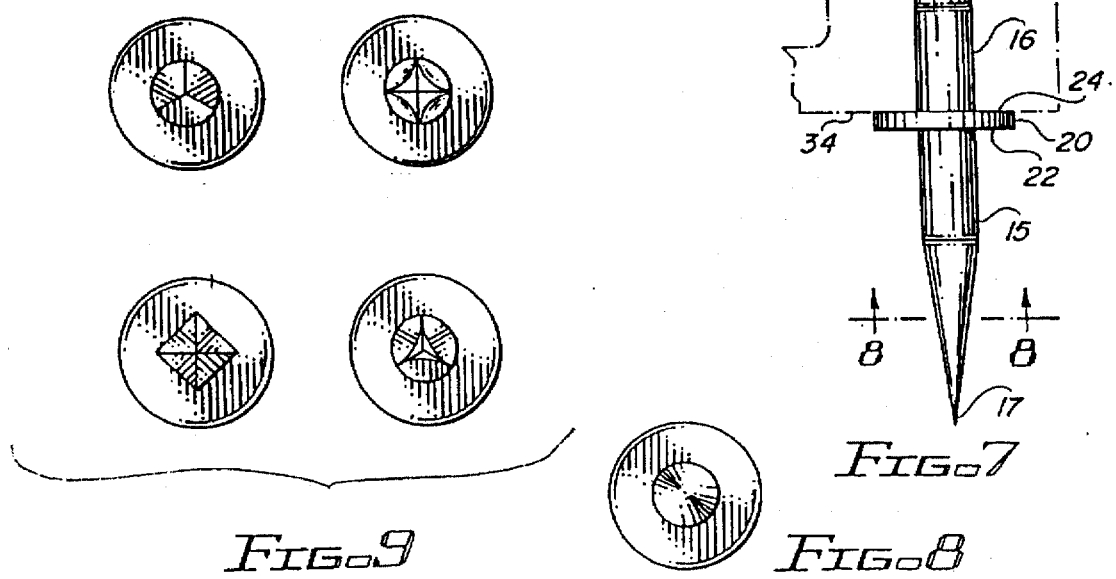

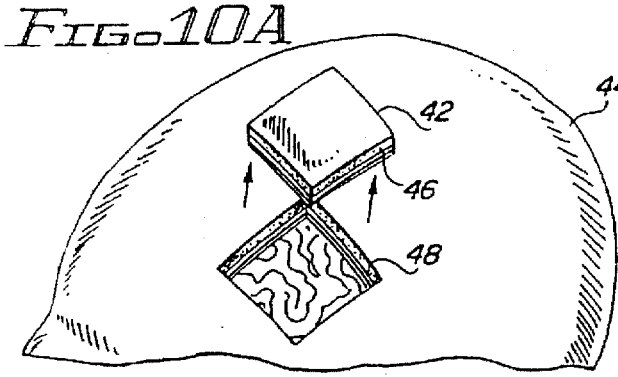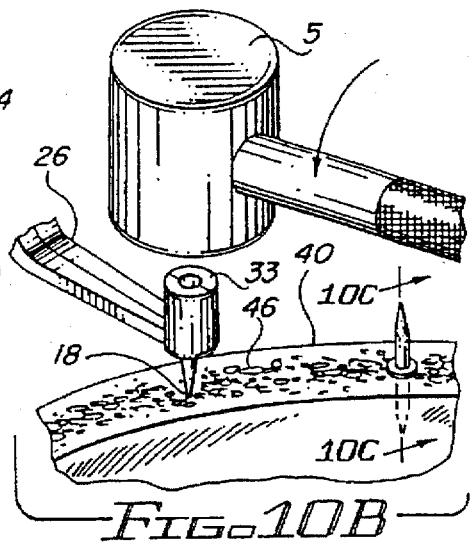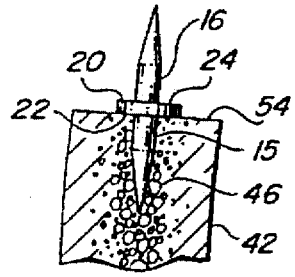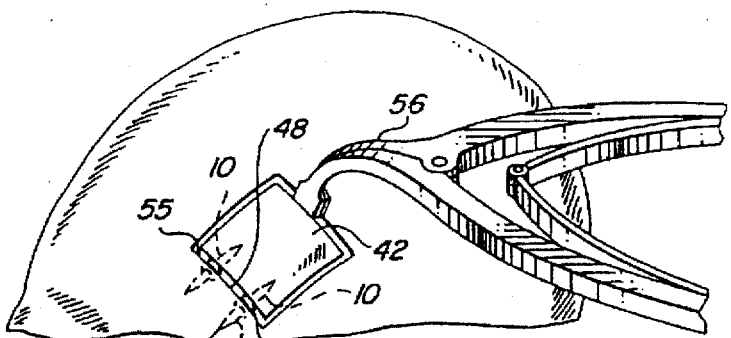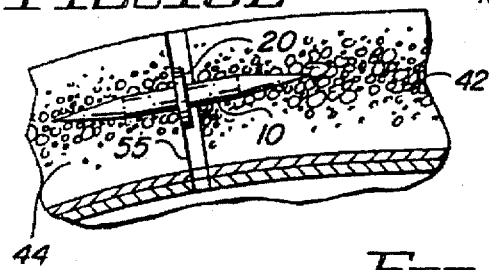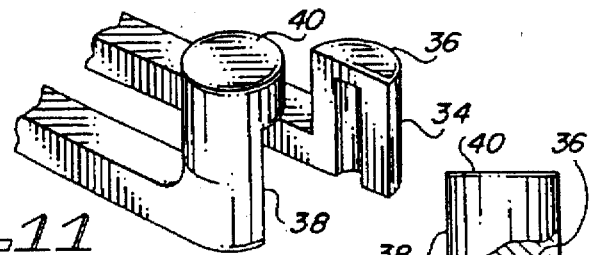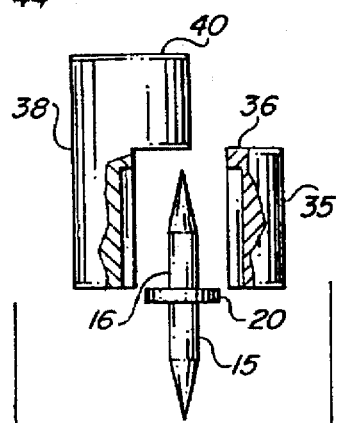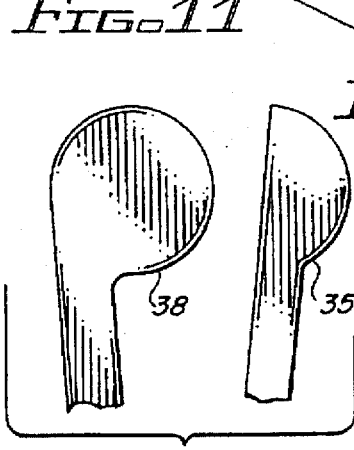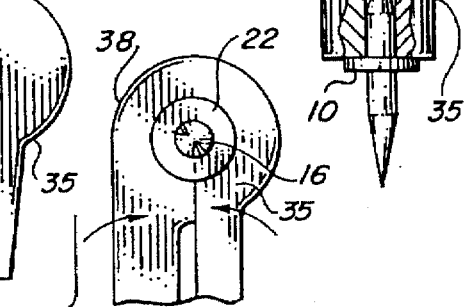

APPARATUS FOR SECURING A CRANIAL PIECE IN POSITION

This application is a continuation of application Ser. No. 08/233,851, filed on Apr. 26, 1994, now U.S. Pat. No. 5,501,685.

BACKGROUND OF THE INVENTION

This invention relates to a apparatus for replacing and securing a cranial piece in position to prevent it from shifting from adjacent bone edges during the process of knitting or healing.

Various surgical procedures require the temporary removal of a cranial piece to permit access to strategic areas of the brain. In order for the cranial piece and cranium to fully knit together and heal following such surgical procedures, the cranial plate or piece must be accurately positioned and secured back in place and all relative movement between opposing bone edges prevented during mending.

Although there are several devices used to rejoin bones other than the cranium, see for example U.S. Pat. Nos. 2,672,861, 4,516,569, 4,858,601 and 4,858,603, none of the devices disclosed in the above-listed patents are adaptable to the relatively thin flat structure of cranial bone. Furthermore, the forces acting on the bones for which the above-described patented devices are intended are quite different from the forces tending to shift cranial pieces out of position in the cranium.

An important disadvantage of prior art technologies and devices is the likelihood of disfigurement. The removed cranial plate frequently extends below the hairline, thus rendering scars visible; the use of prior art screw techniques or metal staples can result in aesthetically unacceptable scar tissue plainly visible on the patient's forehead.

In view of the foregoing, it is therefore an object of the invention to provide a permanent, non-disfiguring apparatus for securing a previously removed cranial plate in position in a cranium to prevent relative movement between opposing bone edges.

A further object of the invention is to provide a method for replacing and securing a cranial plate in position in a cranial opening.

A still further object of the invention is to provide a kit for securing a previously removed cranial plate in position in a cranium to prevent relative movement between opposing bone edges.

SUMMARY OF THE INVENTION

The invention achieves the foregoing objects in one embodiment through the use of a pin adapted to secure a previously removed cranial plate in position in a cranial opening to prevent relative movement between opposing bone edges of the plate and opening. The pin comprises distal and proximal shanks having ends tapering to a relatively sharp point. The shanks are arranged preferably symmetrically about a central collar which has a dimension transverse to the longitudinal axis of the shanks diameter greater than the diameters of the shanks so that the collar forms distal and proximal opposing shoulders for limiting the insertion depth of the pin.

In a second embodiment, a method is provided for replacing and securing a cranial plate in position in a cranial opening. A surgical pin is positioned over a medullar portion of the cranial plate. The pin includes distal and proximal shanks having ends tapering to a relatively sharp point. The shanks are arranged preferably symmetrically about a central collar which has a dimension transverse to the longitudinal axis of the shanks greater than the diameters of the shanks so that the collar forms distal and proximal opposing shoulders for limiting the insertion depth of the pin. The distal tapered shank of the pin is inserted into the medullar portion of the cranial piece so that the distal collar shoulder rests against the medullar portion of the cranial piece. The proximal tapered shank of the pin is inserted into a medullar portion of the opposing cranium so that the proximal collar shoulder rests against the medullar portion of the cranium.

In a third embodiment of the present invention, a kit is provided for securing a previously removed cranial plate in position in a cranium to prevent relative movement between opposing bone edges. The kit includes a surgical pin comprising distal and proximal shanks having ends tapering to a relatively sharp point. The shanks are arranged preferably symmetrically about a central collar which has a dimension transverse to the longitudinal axis of the shanks greater than the diameters of the shanks so that the collar forms distal and proximal opposing shoulders for limiting the insertion depth of the pin. The kit further includes forceps having a distal end forming a chamber for gripping the proximal shank of the pin, the distal end in addition forming a striking surface to permit the pins to be driven into position.

BRIEF DESCRIPTION OF THE DRAWINGS

FIG. 2 illustrates a forceps constructed in accordance with a preferred embodiment of the invention.

FIG. 3 is a more detailed illustration of the distal end of the forceps in a closed position, gripping a surgical pin.

FIG. 4 illustrates the distal end of the forceps in an open position.

FIG. 5 is a top view of the distal end of the forceps illustrated in FIGS. 2–4.

FIG. 6 is a sectional view of the distal end of the forceps shown in FIG. 5, taken on lines 6—6 of FIG. 5.

FIG. 7 is a side view of the distal end of the forceps gripping a surgical pin, as shown in FIG. 3, taken on line 7—7 of FIG. 3.

FIG. 8 is a top view of the distal end of the surgical pin shown in FIG. 7, taken on lines 8—8 of FIG. 7.

FIG. 9 illustrates top views of four alternative embodiments of the distal and proximal shanks of the surgical pin.

FIGS. 10A–10E illustrate a preferred embodiment of the method of the present invention.

FIGS. 11–15 illustrate a second embodiment of the distal end of the forceps.

DESCRIPTION OF THE PREFERRED EMBODIMENTS

Figure 1A:
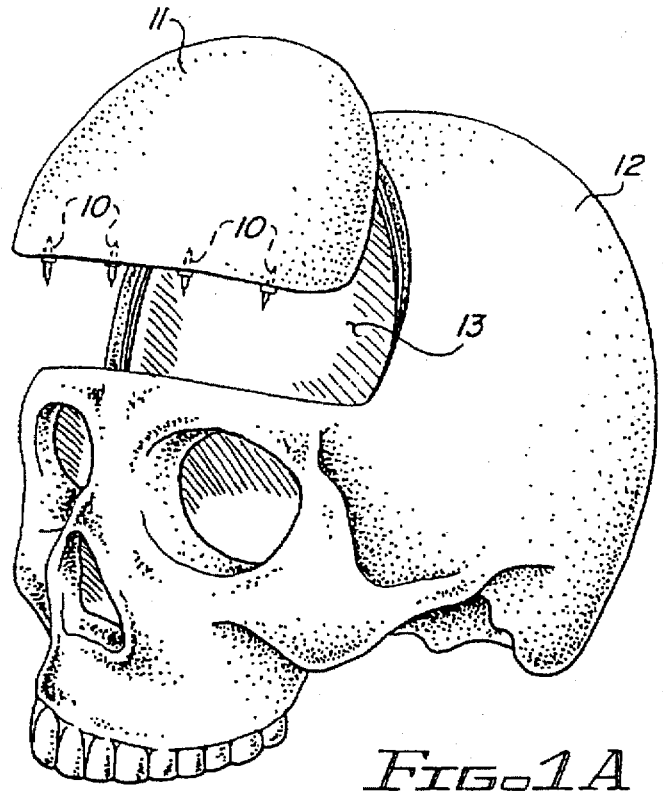
FIG. 1A illustrates a cranial plate removed from a cranium.

FIGS. 1–8 illustrate a first embodiment of an apparatus for securing a previously removed cranial plate in position in a cranial opening to prevent relative movement between opposing bone edges. A surgical pin is indicated generally by reference numeral 10; the surgical pin is constructed of suitable material such as titanium or surgical steel.

Figure 1B:
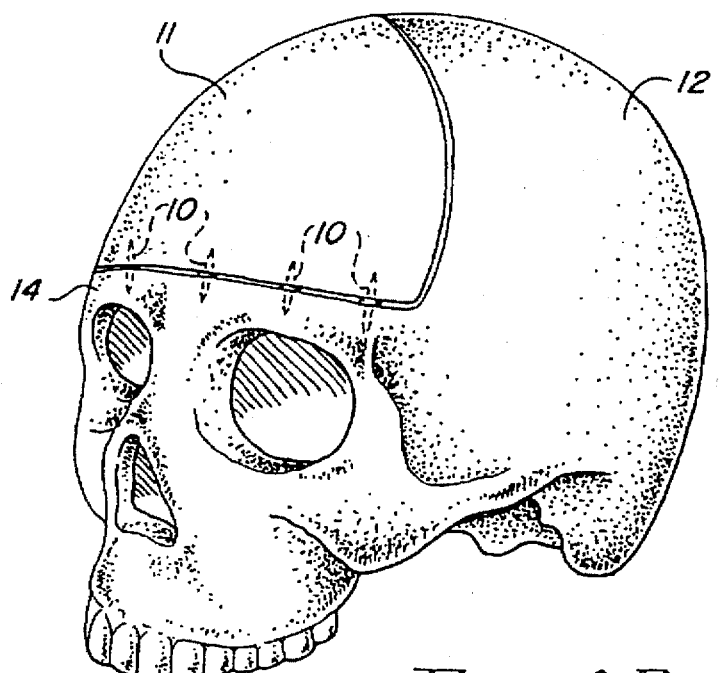
FIG. 1B illustrates the cranial plate of FIG. 9A secured in position in accordance with a preferred embodiment of the invention.

FIG. 1A illustrates a cranial plate 11 removed from a cranium 12, leaving a large cranial opening 13 extending into forehead 14. FIG. 1B illustrates cranial plate 11 of FIG. 1A secured in position in cranium 12 by means of a plurality of pins 10, in accordance with a first embodiment of the present invention.

Pin 10 includes a distal shank 15 and a proximal shank 16; the distal and proximal shanks each have an end, respectively indicated by reference numerals 17 and 18, which tapers to a relatively sharp point; preferably, the taper, expressed as the difference in diameter per millimeter of length, is in the range of from approximately 0.4 millimeter per millimeter of length, to approximately 0.2 millimeter per millimeter of length.

Distal and proximal shanks 15 and 16 are preferably cylindrical and of approximately equal lengths and diameters. FIG. 8 illustrates other acceptable cross-sectional shapes. Depending on the particular circumstances, one shank might have a greater diameter and/or length that the other shank.

Distal and proximal shanks 15 and 16 are arranged, preferably symmetrically, about a central collar 20. Central collar 20 has a dimension 21 transverse to the longitudinal axis of distal and proximal shanks 15 and 16 which dimension is greater than the diameters of the distal and proximal shanks, thereby forming distal and proximal opposing shoulders, respectively indicated by reference numerals 22 and 24, for limiting the insertion depth of pin 10.

Pin 10 can be made in a range of sizes depending on the patient and the particular application. The following dimensions are given for one size to indicate the proportions. Thus, for a typical size, distal and proximal shanks 15 and 16 are each approximately 3 millimeters long, and taper from a diameter of approximately 1 millimeter adjacent each respective shoulder 22 and 24, to a diameter of approximately 0.1 millimeter at the distal and tapered ends 17 and 18, respectively. Central collar 20 has a diameter of approximately 5 millimeters, and is approximately 0.75 millimeters thick.

Also illustrated in FIGS. 2-7 is a forceps 26 having a distal end 28 comprising a pair of opposing semicylindrical members 30. Forceps 26 has the following two functions: to provide means for gripping pin 10 to accurately position it, and to provide a striking surface for use in driving the pin into the proper place. Thus, when semicylindrical members 30 are closed together (as shown, for example, in FIGS. 2-3) they form a cylindrical chamber 32 adapted to grip proximal shank 16 of pin 10, and a striking surface 33. As is best illustrated in FIG. 7, when semicylindrical members 30 are closed together around pin proximal shank 16, proximal shoulder 24 rests against bottom end 34 of forceps distal end 28, and distal shank 15 protrudes therefrom; proximal tapered end 18 is enclosed within cylindrical chamber 32 beneath striking surface 33.

In the alternate embodiment illustrated in FIGS. 11-15, semicylindrical members 30 further include means for covering the top of cylindrical chamber 32 when the semicylindrical members are closed together, providing further protection for the sharp point of proximal tapered end 18. As illustrated in FIG. 11, first alternate semicylindrical member 35 includes a semicircular cap 36 and second alternate semicylindrical member 38 includes a circular cap 40. When first and second alternate semicylindrical members 35 and 38 are closed together as illustrated in FIGS. 13 and 14, semicircular cap 36 covers approximately half of the top of cylindrical chamber 32; circular cap 40 covers both the remaining half of the top of the cylindrical chamber and also the semicircular cap, and provides an alternative striving surface.

The method for replacing and securing a cranial plate 42 in position in a cranial opening 45 will now be described with reference to FIGS. 10A-10E. FIG. 10A illustrates a cranial plate or piece 42 removed from its position in cranium 12, leaving a cranial opening 45. Both cranial plate 42 and cranium 12 contain soft interior marrow, or medullar, portions, referred to respectively by reference numerals 46 and 48.

FIG. 10B illustrates one step of the method of the present invention. The relatively sharp tapered end 17 of distal shank 15 is positioned over cranial plate medullar portion 46 by means of forceps 26; as explained earlier, the forceps include distal end 28 for gripping proximal shank 16 of pin 10. Distal shank 15 is inserted into medullar portion 46 by tapping striking surface 33 of forceps distal end 28 with a striking device such as hammer 52, thereby driving distal tapered end 17 and distal shank 15 into the medullar portion. As is illustrated in FIG. 10C, the depth of penetration of medullar portion 46 by pin 10 is limited by distal shoulder 22, which rests against outer edge 54 of the medullar portion after distal shank 15 has been fully inserted.

Next, as is illustrated in FIG. 10D, proximal shank 16 is inserted into adjacent bone edge 55 of cranium 44 by pushing the relatively sharp proximal tapered end 18 into the appropriate position in cranium medullar portion 48 by means of a tool such as spreader 56. Analogous to insertion of distal shank 15 in cranial piece 42, the depth of penetration of medullar portion 48 by proximal shank 16 is limited by proximal shoulder 24, which rests against outer edge 58 of cranial medullar portion 48 after proximal shank 16 has been fully inserted. As with FIGS. 1A and 1B, FIG. 10D illustrates the likely situation that a plurality of pins 10 will be necessary to secure a cranial piece in a cranium.

As is best illustrated in FIG. 10E, after cranial plate 42 is secured back in its correct position in cranium 44 by means of the present invention, the distance between the cranial plate and opposing cranium bone edge 55 will be the thickness of central collar 20 (approximately 0.75 millimeters), which thickness is kept to a minimum to allow optimal knitting to occur between the cranial piece and the opposing cranium bone edge, and to reduce formation of visible scar tissue.

While the invention has been described with reference to preferred embodiments thereof, the description is for illustrative purposes only and is not to be construed as limiting the scope of the invention. Various modifications and changes may be made by those skilled in the art without departing from the true spirit of the scope of the invention as defined by the appended claims. For example, in the method of the present invention, for some patients it may be necessary to insert pin 10 first into cranium medullar portion 48, followed by insertion of proximal shank 16 into cranial plate medullar portion 46, rather than the opposite, as described above. In addition, although central collar 20 has been depicted as having a circular cross-section, which is preferred, virtually any cross-sectional shape will be suitable. The arrangement of distal and proximal shanks 15 and 16 on central collar 20 need not always be symmetrical, depending on the application.

I claim:

1. A surgical pin for securing a cranial plate in position to prevent the plate from shifting from adjacent bone edges during the process of knitting or healing, said pin comprising:

a cylindrical, distal shank and a cylindrical, proximal shank, each of said shanks having an end tapering to a relatively sharp point, a central collar between the cylindrical portions of said shanks and having a dimension transverse to the longitudinal axis of the shanks greater than the diameters of the shanks, wherein said collar has a diameter approximately equal to the thickness of the medullar portion of the cranial bone for limiting the insertion depth of the pin into the medullar portion of a cranial bone without causing disfigurement and wherein said cylindrical portions and said collar provide gripping surfaces for manipulating said pin and for inserting said pin into the medullar portion of a cranial bone.

2. The surgical pin of claim 1 wherein the distal shank and the proximal shank are of approximately equal lengths and diameters.

3. The surgical pin of claim 2 wherein the taper of the distal and proximal shanks is in the range of from approximately 0.4 millimeter per millimeter of length, to approximately 0.2 millimeter per millimeter of length.

4. A kit for securing a previously removed cranial plate in position in a cranium to prevent relative movement between opposing bone edges while the bone edges heal, the kit comprising:

(a) a surgical pin including a cylindrical, distal shank and a cylindrical, proximal shank each having an end tapering to a relatively sharp point, a central collar between the cylindrical portions of said shanks and having a diameter approximately equal to the thickness of the medullar portion of the cranial bone for limiting the insertion depth of the pin into medullar portions of said opposing bone edges; and (b) forceps having a distal end forming a chamber for gripping the cylindrical portion of the proximal shank.

5. The kit of claim 4 wherein the distal shank and the proximal shank are of approximately equal lengths and diameters, and wherein the distal end of the forceps further forms a striking surface to permit the pin to be driven into position.

6. The kit of claim 5 wherein the taper of the distal and proximal shanks is in the range of from approximately 0.4 millimeter per millimeter of length, to approximately 0.2 millimeter per millimeter of length.

7. The kit of claim 5 wherein the forceps distal end comprises a pair of opposing semicylindrical members which when closed together form a cylindrical chamber adapted to grip the proximal shank of the pin.

8. The kit of claim 7 wherein the semicylindrical members further comprise means for covering the top of the cylindrical chamber when the semicylindrical members are closed together.

* * * * *